(12) United States Patent
Caro et al.

(10) Patent No.: US 9,572,694 B2
(45) Date of Patent: Feb. 21, 2017

(54) HELICAL GRAFT

(71) Applicants: Colin G. Caro, London (GB); Nicholas V. Watkins, London (GB); Spencer J. Sherwin, London (GB)

(72) Inventors: Colin G. Caro, London (GB); Nicholas V. Watkins, London (GB); Spencer J. Sherwin, London (GB)

(73) Assignee: Veryan Medical Limited, Oxford (GB)

( * ) Notice: Subject to any disclaimer, the term of this patent is extended or adjusted under 35 U.S.C. 154(b) by 0 days.

(21) Appl. No.: 14/256,604

(22) Filed: Apr. 18, 2014

(65) Prior Publication Data
US 2014/0225304 A1    Aug. 14, 2014

Related U.S. Application Data

(62) Division of application No. 10/549,498, filed as application No. PCT/GB2004/001156 on Mar. 18, 2004, now abandoned.

(30) Foreign Application Priority Data

Mar. 18, 2003  (GB) .................................. 0306176.9
Jul. 21, 2003   (GB) .................................. 0317004.0
(Continued)

(51) Int. Cl.
*A61F 2/915*  (2013.01)
*A61F 2/91*   (2013.01)
(Continued)

(52) U.S. Cl.
CPC ................ *A61F 2/915* (2013.01); *A61F 2/06* (2013.01); *A61F 2002/068* (2013.01);
(Continued)

(58) Field of Classification Search
CPC .............. A61F 2/06; A61F 2/915; A61F 2/91; A61F 2220/0008; A61F 2220/0016; A61F 2002/823; A61F 2002/91541; A61F 2210/0076; A61F 2/07; A61F 2002/065; A61F 2002/075; A61F 2002/91566; A61F 2/90; A61F 2002/077; A61F 2002/91558; A61F 2230/0054; A61F 2/89; A61F 2002/068; A61F 2002/3008; A61F 2220/005; A61F 2220/0075; A61F 2250/0018; A61F 2250/0036; A61F 2250/0098; A61F 2/82; A61F 2/88; A61F 2002/048; A61F 2002/826; A61F 2002/828; A61F 2002/09
(Continued)

(56) References Cited

U.S. PATENT DOCUMENTS 4,596,548 A   6/1986   DeVries et al.
4,604,762 A   8/1986   Robinson
(Continued)

FOREIGN PATENT DOCUMENTS

EP    0 275 230 A2    7/1988
EP    0 696 447 A2    2/1996
(Continued)

OTHER PUBLICATIONS

Caro et al., "Influence of Non-Planar Geometry on Flow Separation" (1998) J. Physiol. 513P, 2P.
(Continued)

*Primary Examiner* — Christian Sevilla
*Assistant Examiner* — Seema Mathew
(74) *Attorney, Agent, or Firm* — Fay Sharpe LLP

(57) ABSTRACT

A graft includes a flow tubing having a tubing portion defining a flow lumen. The flow lumen of the tubing portion is substantially free of ribs or grooves. A center line of the
(Continued)

flow lumen follows a substantially helical path with a helix angle less than or equal to 65°. The amplitude of the helix is less than or equal to one half of the internal diameter of the tubing portion.

19 Claims, 13 Drawing Sheets

(30) Foreign Application Priority Data

Sep. 11, 2003 (GB) .................................. 0321327.9
Dec. 11, 2003 (GB) .................................. 0328757.0

(51) Int. Cl.
*A61F 2/06* (2013.01)
*B29C 53/14* (2006.01)
*B29C 65/00* (2006.01)

(52) U.S. Cl.
CPC ............... *A61F 2002/91508* (2013.01); *A61F 2002/91516* (2013.01); *B29C 53/14* (2013.01); *B29C 65/00* (2013.01)

(58) Field of Classification Search
USPC ........................................................ 623/1.22
See application file for complete search history.

(56) References Cited

U.S. PATENT DOCUMENTS

| | | | |
|---|---|---|---|
| 5,156,619 A | 10/1992 | Ehrenfeld | |
| 5,295,959 A | 3/1994 | Gurbel et al. | |
| 5,308,356 A | 5/1994 | Blackshear, Jr. et al. | |
| 5,370,691 A | 12/1994 | Samson | |
| 5,383,856 A | 1/1995 | Bersin | |
| 5,484,411 A | 1/1996 | Inderbitzen et al. | |
| 5,545,132 A | 8/1996 | Fagan et al. | |
| 5,569,191 A | 10/1996 | Meyer | |
| 5,596,990 A | 1/1997 | Yock et al. | |
| 5,618,299 A | 4/1997 | Khosravi et al. | |
| 5,649,978 A | 7/1997 | Samson | |
| 5,653,745 A | 8/1997 | Trescony | |
| 5,670,161 A | 9/1997 | Healy et al. | |
| 5,733,327 A | 3/1998 | Igaki et al. | |
| 5,735,816 A | 4/1998 | Lieber et al. | |
| 5,800,456 A | 9/1998 | Maeda et al. | |
| 5,865,723 A | 2/1999 | Love | |
| 6,039,754 A | 3/2000 | Caro | |
| 6,152,139 A | 11/2000 | Laufer | |
| 6,364,904 B1 | 4/2002 | Smith | |
| 6,375,660 B1 | 4/2002 | Fischell et al. | |
| 6,425,908 B2 | 7/2002 | Ravenscroft et al. | |
| 6,527,739 B1 | 3/2003 | Bigus et al. | |
| 6,896,007 B2 | 5/2005 | Cymbalisty | |
| 2001/0049549 A1 | 12/2001 | Boylan et al. | |
| 2002/0022877 A1 | 2/2002 | Mueller et al. | |
| 2002/0035390 A1 | 3/2002 | Schaldach et al. | |
| 2002/0049487 A1 | 4/2002 | Lootz et al. | |
| 2002/0077693 A1* | 6/2002 | Barclay ................ | A61F 2/88 623/1.13 |
| 2002/0116044 A1 | 8/2002 | Cottone, Jr. et al. | |
| 2002/0179166 A1* | 12/2002 | Houston ................ | A61F 2/06 138/39 |
| 2003/0163154 A1 | 8/2003 | Miyata et al. | |
| 2004/0039443 A1 | 2/2004 | Solem et al. | |
| 2006/0047334 A1 | 3/2006 | Houston et al. | |
| 2006/0122554 A1 | 6/2006 | Wilk | |
| 2006/0124187 A1 | 6/2006 | Houston et al. | |
| 2006/0265051 A1* | 11/2006 | Caro ................ | A61F 2/07 623/1.17 |
| 2007/0021707 A1* | 1/2007 | Caro ................ | A61F 2/06 604/8 |
| 2007/0028984 A1* | 2/2007 | Caro ................ | B01J 8/062 138/177 |
| 2007/0112407 A1 | 5/2007 | Mertens et al. | |
| 2007/0156078 A1 | 7/2007 | Caro et al. | |
| 2007/0213663 A1 | 9/2007 | Wang | |
| 2008/0262599 A1* | 10/2008 | Caro ................ | A61F 2/82 623/1.16 |
| 2008/0306440 A1 | 12/2008 | Hirszowicz et al. | |
| 2009/0293574 A1* | 12/2009 | Caro ................ | A61F 2/06 72/364 |
| 2010/0094403 A1* | 4/2010 | Heraty ................ | A61F 2/958 623/1.15 |
| 2011/0040371 A1* | 2/2011 | Hanssen ................ | A61F 2/88 623/1.22 |
| 2012/0016460 A1* | 1/2012 | Heraty ................ | A61F 2/91 623/1.15 |
| 2014/0039605 A1* | 2/2014 | Caro ................ | A61F 2/88 623/1.16 |
| 2014/0277352 A1* | 9/2014 | Caro ................ | A61F 2/82 623/1.11 |

FOREIGN PATENT DOCUMENTS

| | | |
|---|---|---|
| EP | 0 699 423 A2 | 3/1996 |
| EP | 0 714 640 A1 | 6/1996 |
| EP | 0 581 900 B1 | 2/1998 |
| EP | 0 612 536 B1 | 12/1999 |
| EP | 1 042 997 A1 | 10/2000 |
| EP | 1 127 557 A1 | 8/2001 |
| EP | 1 254 645 A1 | 11/2002 |
| EP | 1 269 935 A2 | 1/2003 |
| EP | 1 270 040 A1 | 1/2003 |
| EP | 1 279 382 A1 | 1/2003 |
| EP | 2 292 183 A1 | 3/2011 |
| FR | 2 248 015 A1 | 5/1975 |
| FR | 2 657 945 A3 | 8/1991 |
| FR | 2 666 502 A1 | 3/1992 |
| GB | 2 092 894 A | 8/1982 |
| GB | 2 298 577 A | 9/1996 |
| GB | 2 344 053 A | 5/2000 |
| GB | 2 425 485 A | 11/2006 |
| JP | 07-507697 | 8/1995 |
| JP | 08-215317 | 8/1996 |
| JP | 08-257139 | 10/1996 |
| JP | H11-506628 A | 6/1999 |
| JP | 2001-252987 | 9/2001 |
| JP | 2003-528689 A | 9/2003 |
| JP | 2005-103321 A | 4/2005 |
| JP | 2006-520630 | 9/2006 |
| WO | WO 95/09585 A1 | 4/1995 |
| WO | WO 95/17223 A1 | 6/1995 |
| WO | WO 95/35072 A2 | 12/1995 |
| WO | WO 97/24081 A1 | 7/1997 |
| WO | WO 98/26731 A2 | 6/1998 |
| WO | WO 98/26731 A3 | 6/1998 |
| WO | WO 98/53764 A2 | 12/1998 |
| WO | WO 99/17682 A1 | 4/1999 |
| WO | WO 00/32241 A1 | 6/2000 |
| WO | WO 00/38591 A2 | 7/2000 |
| WO | WO 00/38591 A3 | 7/2000 |
| WO | WO 00/48530 A1 | 8/2000 |
| WO | WO 00/49973 A2 | 8/2000 |
| WO | WO 01/45593 A1 | 6/2001 |
| WO | WO 01/74270 A2 | 10/2001 |
| WO | WO 01/89420 A2 | 11/2001 |
| WO | WO 02/066095 A2 | 8/2002 |
| WO | WO 02/098325 A2 | 12/2002 |
| WO | WO 03/000157 A1 | 1/2003 |
| WO | WO 03/045278 A1 | 6/2003 |
| WO | WO 03/103540 A1 | 12/2003 |
| WO | WO 2004/047908 A2 | 6/2004 |
| WO | WO 2004/066852 A2 | 8/2004 |
| WO | WO 2004/082533 A1 | 9/2004 |
| WO | WO 2008/117256 A2 | 10/2008 |

OTHER PUBLICATIONS

Duerig et al., "A Comparison of Balloon- and Self-Expanding Stents", Min Invas Ther & Allied Technol 2002: 11(4) pp. 173-178.

(56) References Cited

OTHER PUBLICATIONS

Stoeckel et al., "A Survey of Stent Designs", Min Invas Ther & Allied Technol 2002: 11(4) pp. 137-147.
Vijayan et al., "External Supports and the Prevention of Neointima Formation in Vein Grafts", Eur. J. Vasc. Endovasc. Surg 24, pp. 13-22 (2002).

* cited by examiner

HELICAL GRAFT

This application is a divisional application of U.S. Ser. No. 10/549,498 which was filed on Aug. 14, 2006 and is still pending.

BACKGROUND OF THE DISCLOSURE

This invention relates to grafts.

We have previously proposed that the flow pattern in arteries including the swirling pattern induced by their non-planar geometry operates to inhibit the development of vascular diseases such as thrombosis, atherosclerosis and intimal hyperplasia.

It is known from WO 95/09585 to provide a vascular prosthesis comprising a length of generally hollow tubing having openings at both ends thereof and including a non-planar curved portion so as to induce swirl flow in blood flowing through the curved portion. As explained in that publication, the swirl flow induced by skewing of the blood flow within the non-planar curved portion improves flow characteristics and reduces the potential for deposit build-up and vascular disease including intimal hyperplasia.

In WO 98/53764, there is disclosed a stent for supporting part of a blood vessel. The stent includes a supporting portion around which or within which part of a blood vessel intended for grafting can be placed so that the stent internally or externally supports that part. The supporting portion of the stent is shaped so that flow between graft and host vessel is caused to follow a non-planar curve. This generates a swirl flow, again to provide a favourable blood flow velocity pattern which reduces the occurrence of vascular disease, particularly intimal hyperplasia.

In WO 00/32241, there is disclosed another type of stent, in this case including a supporting portion around which or within which part of an intact blood vessel other than a graft can be placed. This supporting portion can prevent failure of the vessel through blockage, kinking or collapse. Again, the supporting portion of the stent is of a shape and/or orientation whereby flow within the vessel is caused to follow a non-planar curve. Favourable blood flow velocity patterns can be achieved through generation therein of swirl flow within and beyond the stent. Failures in blood vessels through diseases such as thrombosis, atherosclerosis, intimal hyperplasia can be significantly reduced.

Further aspects of how swirl flow is beneficial are explained in the above publications. It is further explained in Caro et al. (1998) J. Physiol. 513P, 2P how non-planar geometry of tubing inhibits flow instability.

In certain embodiments of the above publications the artificial or modified natural blood flow tubing is helical or part-helical. In the case of part-helical tubing, the prosthesis or the supported vessel may undergo less than one complete turn of a helix, for example less than one half or less than one quarter of such a turn.

In this specification, the "swept width" of a helix means the outer width of the helix when viewed axially of the helix. In cases where this swept width is relatively wide compared to the width of the tubing itself, the prosthesis or stent may be more bulky than is necessary or acceptable to induce the required swirl flow.

It has been proposed in WO 00/38591 to use internal helical grooving or ridging to induce helical flow. Similar proposals have been made in WO 97/24081 and EP 1127557 A1. However, the use of ribs or grooves in an otherwise cylindrical tube may not reliably induce swirl flow across the entire cross-section of flow. There may be a tendency for the flow nearer to the centre of the tube to follow a linear path, particularly for flows at higher Reynolds numbers. Furthermore, the ratio of the wetted perimeter to the cross-sectional area of a tube is increased by the provision of ridges or grooves. There is a departure from a circular cross-sectional shape. This may lead to increased flow resistance and a consequent pressure loss, and damage to blood vessels and blood cells and the development of pathology.

It is also proposed in WO 00/38591 to use a non-circular cross-section tube which is twisted. Again, however, a departure from circularity increases the ratio of the wetted perimeter to the cross-sectional area and will have disadvantages.

A further proposal in WO 00/38591 is to provide a circular-section tube bent into a cork screw shape. It is usual for the helix of a cork screw to have a clear gap down the middle, so that this proposed configuration would have a wide swept width compared to the width of the tubing, certainly more than two tubing diameters. The amplitude of the helix would be greater than one half of the internal diameter of the tubing and there would be no "line of sight" along the inside of the tubing. This proposal would therefore be relatively bulky and unsuitable for certain applications. A similar proposal is shown in FIG. 5 of WO 02/98325, the tubing having a helix with a large amplitude and again no "line of sight" along the inside of the tubing.

Various designs of elastomeric arterial graft prostheses are proposed in GB 2092894. In the version of FIG. 8 of that document, the interior surface is undulatory or corrugated, with different undulations either having parallel circumferential paths or joined in a "spiral" path. The corrugations are proposed as an alternative to reinforcement for improving the anti-kinking characteristics of the graft. In the case of the "spiral" corrugations which appear to be shown in FIG. 8, the angle of the corrugations to the longitudinal axis is relatively high, of the order of more than 70°. This is to be expected where the purpose of the corrugations is to improve anti-kinking or other structural characteristics, rather than for reasons relating to the nature of the blood flow through the graft. In fact, it is likely that the corrugations would tend to cause the flow to undergo sharp changes of direction leading to flow separation and the creation of stagnant near-wall regions.

BRIEF SUMMARY

According to a first aspect of the invention, there is provided a graft comprising flow tubing having a tubing portion defining a flow lumen, the flow lumen of said tubing portion being substantially free of ribs or grooves, wherein the centre line of the flow lumen follows a substantially helical path with a helix angle less than or equal to 65°, and wherein the amplitude of the helix is less than or equal to one half of the internal diameter of the tubing portion.

The invention is particularly suitable for in vivo tubing, such as vascular prostheses. It is very suitable for vascular access grafts because (unlike with tubing having a large amplitude helix relative to its internal diameter) the tubing can be readily punctured with a needle to allow blood to be withdrawn and returned for e.g. dialysis.

The graft according to the invention improves flow characteristics. As is well known, in the case of straight, tubes, near wall velocities are very low compared to velocities at the core of the tube, due to the effects of viscosity. In the case of tubes which are bent in a single plane, the speed of the flow at the outside of the bend is increased but the speed of the flow at the inside is retarded further. In both cases, there is considerable variation in axial velocity across the width of the tube. With the use of a helical tubing portion according to the invention, a swirl flow is generated and the axial velocity profile of the flow across the tubing portion becomes generally more uniform or "blunter", with the axial velocity of flow at both the outside and inside of the tubing portion being closer to the mean axial velocity.

Thus, the flow characteristics are improved by causing swirling and a relatively uniform distribution of axial and near wall velocity. Mixing over the cross section is also promoted and there is a reduction in the likelihood of occurrence of flow instability. The avoidance and flushing of stagnant zones is assisted. There is a reduction in the potential for deposit build up within and downstream of the graft and the development of pathology.

In this specification, the amplitude of the helix refers to the extent of displacement from a mean position to a lateral extreme. So, in the case of the tubing having a helical centre line, the amplitude is one half of the full lateral width of the helical centre line.

In the tubing of the first aspect of the invention, in which the amplitude of the helix is less than or equal to one half of the internal diameter of the tubing, there is a "line of sight" along the lumen of the tubing, unlike in the case of a corkscrew configuration where in effect the helix is wound around a core (either solid, or "virtual" with a core of air). We have found that the flow at the line of sight generally has a swirl component, even though it could potentially follow a straight path.

For the purposes of this specification, the term "relative amplitude" of a helical tubing is regarded as the amplitude divided by the internal diameter. So, in the tubing of the first aspect of the invention in which the amplitude of the helical tubing is less than or equal to one half of the internal diameter of the tubing, this means that the relative amplitude is less than or equal to 0.5. Relative amplitudes less than or equal to 0.45, 0.4, 0.35, 0.3, 0.25, 0.2, 0.15 or 0.1 may be preferred in some circumstances. It is however preferred for the relative amplitude to be at least 0.05, more preferably 0.1. This can help to ensure that the desired swirl flow is induced.

The relative amplitude may vary according to the use of the tubing and the spatial constraints on its design. It will however be appreciated that by keeping the amplitude less than half the tubing internal diameter a swirling flow may be induced without creating an excessively large device. The "envelope" occupied by the graft can fit into the space available in the surrounding tissue, and even if this envelope is caused to follow a particular path by the local environment in which the graft is located, the desired helical geometry of the flow lumen can be maintained.

The angle of the helix is also a relevant factor in balancing the space constraints on the flow tubing with the desirability of maximising the cross-sectional area available for flow. The helix angle is less than or equal to 65°, preferably less than or equal to 55°, 45°, 35°, 25°, 20°, 15°, 10° or 5°. As with relative amplitudes, the helix angle may be optimized according to the conditions: viscosity, density and velocity of fluid.

Generally speaking, for higher Reynolds numbers the helix angle may be smaller whilst satisfactory swirl flow is achieved, whilst with lower Reynolds numbers a higher helix angle will be required to produce satisfactory swirl. The use of higher helix angles will generally be undesirable, as there may be near wall pockets of stagnant fluid. Therefore, for a given Reynolds number (or range of Reynolds numbers), the helix angle will preferably be chosen to be as low as possible to produce satisfactory swirl. Lower helix angles result in smaller increases in length as compared to that of the equivalent cylindrical tubing. In certain embodiments, the helix angle is less than 20° or less than 15°.

It will be appreciated that in pulsatile flow, the Reynolds number will vary over a range. Typical mean resting arterial blood flow Reynolds numbers are about 100, reaching peak values of two or three times that in pulsatile flow and three to four times the mean during exertion. Therefore the extent to which swirl flow is promoted will vary likewise. Even if there are stagnant flow regions at lower Reynolds numbers, because for example a low helix angle and/or a low relative amplitude has been selected, these will tend to be flushed out during periods of flow when the Reynolds numbers are higher.

The tubing portion may be made with substantially the same relative amplitude and helix angle along its length. There may be small variations when the tubing is in use, caused by elongation or contraction of the tubing portion due to tensile loading or caused by torsional loading. However, there may be circumstances in which the tubing portion has a variable helix angle and/or relative amplitude, either to suit the space constraints or to optimise the flow conditions.

For reasons of manufacturing simplicity, it may be preferred for the tubing portion to have a substantially constant cross-sectional area along its length. Again, there may be variations in use caused by loading on the tubing portion.

The helical tubing portion may form just part of the overall length of tubing or it may extend over substantially its entire length. For example, a prosthesis may have a tubing portion with the geometry of the invention over part of its length or over substantially its entire length.

The helical tubing portion may undergo a fraction of one complete turn, for example one quarter, one half or three quarters of a turn. Preferably, the helical tubing portion undergoes at least one turn, more preferably at least a plurality of turns. Repeated turns of the helix along the tubing portion will tend to ensure that the swirl flow is generated and maintained.

The tubing, including the tubing portion, may extend generally linearly. In other words, the axis about which the centre line of the tubing portion follows a substantially helical path, may be straight. Alternatively the axis may itself be curved, whereby the envelope occupied by the tubing is curved, for example to produce an "arch" shaped tubing. The bend of the arch may be planar or non-planar, but should preferably be such that swirl is maintained and not cancelled by the geometry of the bend. Thus, for example, a prosthesis may be generally "arch" shaped (planar or non-planar), having the geometry in accordance with the first aspect of the invention, i.e. being in the form of a tubing portion following a substantially helical path with a helix angle less than or equal to 65°, and with an amplitude less than or equal to one half of the internal diameter of the tubing portion.

In general, the helical centre line of the tubing portion is defined by the tubing portion itself and is not due to a branch in the tubing. The tubing portion may interface with another portion or a branch which may be planar or non-planar. The interface between the helix of the tubing portion and the branch will preferably be such that swirl is maintained, and that there is not a tendency for the swirl to be cancelled by the geometry of the branch.

The tubing may if desired comprise a pharmaceutical coating. Such a coating could be provided to provide sustained release of the pharmaceutical over a period of time.

So, the blood flow tubing could provide a pharmaceutical for initial treatment of a disease, and in the longer term the tubing portion gives a therapeutic benefit due to the characteristics which it imparts to the flow.

In the above prior art proposals using multiple grooves or ridges arranged about the tubing circumference, or non-circular sections which are twisted, where the tubing is substantially straight, then the centre line of the tubing is also straight. This is unlike the centre line of the tubing portion of the present invention, in its first aspect, which follows a substantially helical path. Thus, the tubing portion of the invention may have a circular cross-section and thus the smallest possible wetted perimeter to cross-sectional area ratio, whilst still having the necessary characteristics to induce swirl flow. Of course, there may be circumstances in which the tubing portion of the present invention has a non-circular cross-section, for example to assist interfacing or where pressure loss considerations are not significant.

In the proposals of WO 97/24081 and EP 1127557 A1, the tubing has a single internal rib arranged helically. This results in the tubing having a centre line which follows a helical path, but because the rib is provided in an otherwise cylindrical tube, the amplitude of the helix is very small, generally having a relative amplitude appreciably less than 0.05. The generation of swirl flow, if there is any, is correspondingly limited and unsatisfactory.

Further concerning the prior art proposals using grooves or ridges or ribs, it should be noted that arterial geometry is under normal physiological conditions non-planar (i. e. curved in more than one plane in the nature of a helix) and not grooved or rifled. We have found experimentally that at higher relevant Reynolds numbers, the flow in a helical (non-planar) geometry differs from that in a rifled/grooved geometry, e.g. there is swirling of both near-wall flow and core flow in the former case. The development of swirl flow is more rapid than in the case of rifled/grooved tubing, where swirl flow can take many tubing diameters to develop. Thus, there is the expectation that the introduction of the physiological non-planar geometry (unlike grooved or rifled geometry) will be beneficial in respect of inhibiting the development of pathology.

Because the tubing portion of the invention has a helical centre line, there is spatial reorganisation of vortical structures, which results in motion of the core or cores of the axial flow across the section of the tubing portion, promoting mixing across the cross section. The swirl inhibits the development of stagnation and flow separation regions and stabilises flows.

As mentioned, in the case of the prior art proposals using multiple grooves or ridges or ribs, or twisted tubes of a non-circular cross-section, the centre line is straight, not helical. Whilst this can be expected to stabilise flow at sharp bends, it does not in straight tubes cause spatial reorganisation of vortical structures, resulting in motion of the core or cores of the axial flow across the section of the tube. Thus it does not promote mixing across the cross section to the same extent as tubing according to the invention. Such mixing may be important in maintaining the mass transport and physiological integrity of the blood vessels.

According to another aspect of the invention, there is provided a graft comprising flow tubing having a tubing portion defining a flow lumen, wherein the centre line of the flow lumen follows a substantially helical path with a helix angle less than or equal to 65°, wherein the amplitude of the helical centre line is less than or equal to one half of the internal diameter of the tubing portion, and wherein the amplitude of the helical centre line is more than or equal to 0.05 of the internal diameter of the tubing portion. The various other possible features of the graft discussed herein may be provided in the graft of this aspect of the invention.

The tubing geometry disclosed herein may be used in various biomedical applications e.g. in various arteries (such as in the coronary and renal arteries), in veins, and in non-cardiovascular applications such as in the gastro-intestinal (e.g. bile or pancreatic ducts), genito-urinary (e.g. ureter or urethra) or the respiratory system (lung airways). Thus, the invention extends to flow tubing for body fluids other than blood. In general, the use of the tubing geometry of the invention can avoid the presence of stagnant regions, and hence be beneficial.

If tubing is made from flexible material, such as synthetic fabric, but rather than being formed as a cylinder is instead formed so that its centre line follows a substantially helical path, it is in some circumstances capable of "straightening out", involving a reduction in the amplitude of the helix and a corresponding increase in the pitch of the helix and in the length of the tubing (i.e. axial extension). The benefits of swirl flow discussed above may then be reduced or lost.

According to another aspect of the invention there is provided a graft comprising flow tubing having a tubing portion, the tubing portion comprising a wall defining a longitudinally extending flow lumen which is substantially free of ribs or grooves, the flow lumen having a centre line following a substantially helical path, and the wall having a helical portion extending longitudinally and circumferentially so as to resist reduction of the amplitude of the helical centre line.

A helical portion according to this aspect of the invention can therefore help to maintain the desired amplitude of the helical centre line, and hence maintain the desired swirl fluid flow characteristics.

There are a number of situations where tubing could be subjected to "straightening out" effects tending to cause helical amplitude reduction. These include internal pressurisation by a fluid, for example in response to arterial pressure, or axial extension if the graft is used in the vicinity of a joint, or a combination of the two. Although there may still be a reduction in amplitude when the tubing is subjected to such straightening out forces, the amount of this reduction is less than would be the case without the helical portion.

In general, the helical portion will have a lower extensibility as compared to adjacent portions of the tubing. It will normally have the same pitch as the helical centre line of the flow lumen so as to conform therewith.

The invention is particularly suitable for in vivo tubing, such as vascular prostheses, and for vascular access grafts.

The longitudinal cavity of the tubing wall itself provides the lumen for body fluid flow. The fluid may then act directly on the tubing wall and create the internal pressurisation tending to straighten out (i.e. to increase the pitch and reduce the helical amplitude) the tubing and hence the lumen. This is resisted by the helical portion.

The helical portion may be thicker in the radial direction than adjacent portions of the tubing wall. This is a way of achieving the result of the helical portion having lower extensibility than the adjacent portions. Alternatively or additionally, the helical portion may be made from a material different from that of adjacent portions of the tubing wall.

In order to avoid excessive lateral bulk, the amplitude of the helical centre line of the tubing longitudinal flow lumen, once internally pressurised, may be less than or equal to one half of the internal diameter of the tubing. It is expected that any straightening out of the tubing, and hence reduction in the relative amplitude, when the tubing is in use will not be significant, because of the presence of the helical portion.

The various other possible features of the graft discussed herein (such as in relation to the amplitude of the helical centre line, the helix angle, the constance or variation of the amplitude or the helix angle, the number of turns and so forth) may be provided in the graft of this aspect of the invention.

The invention also extends to methods of manufacturing grafts.

According to another aspect of the invention, therefore, there is provided a method of making a graft, the method comprising positioning a generally tubular, flexible wall adjacent to a further flexible member, twisting the tubular flexible wall and the flexible member around each other, and causing the tubular flexible wall to retain, at least partly, the twisted shape.

By using a flexible member, the amplitude of the twisted tubular wall can be kept desirably small, so as to form tubing without excessive lateral bulk. If the tubular wall were instead twisted round a rigid member, then it would adopt a corkscrew configuration, in effect a helix round a core provided by the rigid member. If the tubular wall retained that shape when the rigid member is removed, it would then have a core of air and be laterally bulky.

In general, the tubular wall formed by twisting round a flexible member will define a longitudinally extending cavity having a centre line following a substantially helical path. The relative amplitude of helical tubing formed by the method discussed is preferably less than or equal to 0.5. The tubing may have relative amplitudes, helix angles, cross-sectional shapes, number of turns et cetera as discussed above in relation to the other aspects of the invention.

It will generally be undesirable for the cross-sectional shape of the tubular wall to be distorted, for example flattened, during twisting. Therefore, the tubular wall may be reinforced to assist it in maintaining its cross-sectional shape during twisting with the flexible member. The reinforcement may be integral with or adherent to the tubular wall, for example comprising a helical winding with a large helix angle, as is known for example from GB 2298577. Alternatively, or additionally, it may be desirable to provide reinforcement in the form of internal support for the tubular wall during twisting of the tubular wall. A flexible rod or tube or a spring may be inserted into the tubular wall to provide internal support and removed after the desired geometry has been at least partly retained.

A preferred cross-sectional shape of the longitudinally extending helical cavity is substantially circular. If reinforcement is provided, it may then help the tubular wall to keep to this shape.

The further flexible member may for example be another generally tubular, flexible wall. This may be reinforced if necessary to assist it in maintaining its cross-sectional shape.

The step of at least partially retaining the twisted shape may comprise thermosetting the tubular flexible wall and allowing it to cool.

It has been found that tubing made by the above method need not have a helical portion extending longitudinally and circumferentially of the wall to help resist reduction of the amplitude of the helical centre line. For example, tubing made of ePTFE (expanded polytetrafluoroethylene) and of a conventional type for use as vascular prostheses has been found generally to retain the desired geometry without the need for a helical portion acting as "reinforcement". However, for tubing made of other biocompatible materials, in view of the potential straightening out effects on tubing having a twisted shape when the tubing is in use, it may be preferred to provide the tubing flexible wall with a helical portion extending longitudinally and circumferentially and for assisting in retaining the twisted shape. In order that the helical portion will complement the twisted shape achieved by the twisting step, it is preferably positioned to lie adjacent to the flexible member (for example in contact therewith).

According to another aspect of the invention, there is provided a method of making a graft, the method comprising providing a helical mandrel having a centre line following a substantially helical path, providing a generally tubular, flexible wall having a longitudinally extending cavity, positioning the tubular wall adjacent to the helical mandrel to cause the longitudinally extending cavity to have a centre line following a substantially helical path, and causing the tubular wall to retain, at least partly, the shape with the longitudinally extending helical cavity.

With this manufacturing method it is not necessary to use a flexible member as the mandrel and the helical mandrel may be substantially rigid. This enables the geometry of the helical mandrel to be fixed in advance of its use with the tubular wall to make the graft, so facilitating consistent production of grafts to a predetermined specification.

Preferably the helical mandrel extends longitudinally and circumferentially around a cylindrical space which defines a core of the helical mandrel, and the outside diameter of the tubular wall is greater than the diameter of the core of the helical mandrel.

The tubular wall may be reinforced to assist it in maintaining its cross-sectional shape. The reinforcement may be integral with or adherent to the wall. Alternatively, or additionally, the tubular wall may be reinforced by a removable internal support.

The method is suited to a continuous production process. The tubular wall may be fed to one end of the helical mandrel and, following deformation to the desired shape, it may separate from the helical mandrel at the other end thereof. Preferably, therefore, the tubular wall and the helical mandrel are moved in the longitudinal direction relative to each other.

The graft made by the above method may comprise the various other possible features of grafts discussed herein, such as in relation to the amplitude of the helical centre line, the helix angle, the constance or variation of the amplitude or the helix angle, the number of turns and so forth.

According to a further aspect of the invention, there is provided a method of making a graft, the method comprising providing a mandrel, providing a generally tubular, flexible wall having a longitudinally extending cavity, winding the tubular wall around the mandrel to extend circumferentially and longitudinally thereof so as to cause the tubular wall to define a first shape in which its longitudinally extending cavity has a centre line following a substantially helical path, setting the tubular wall, and separating the tubular wall from the mandrel so as to allow the amplitude of the helical centre line to reduce whereby the tubular wall adopts a second shape in which the amplitude of the helical centre line is less than or equal to one half of the internal diameter of the tubular wall.

This aspect of the invention allows a straight and generally rigid mandrel to be used, without creating a graft of excessive lateral bulk. Preferably, the mandrel comprises guide means to aid the winding of the tubular wall around the mandrel. Such a guide means can be used to ensure that grafts are made to the same helix angle each time the mandrel is used.

The setting of the tubular wall is preferably a thermosetting step. If the material of the tubular wall is ePTFE, for example, this will adopt a first shape and then, upon separation from the mandrel, adopt the second shape with a reduced helical amplitude.

As with other methods described herein, it may be desirable to reinforce the tubular wall to assist it in maintaining its cross-sectional shape.

According to a further aspect of the invention, there is provided a method of making a graft, the method comprising arranging an elongate member helically along a generally tubular, flexible wall so that the elongate member extends longitudinally and circumferentially of the tubular wall, tensioning the elongate member to cause the wall to define a longitudinally extending cavity having a centre line following a substantially helical path, and causing the wall to retain, at least partly, the shape with the longitudinally extending helical cavity.

The helically arranged elongate member thus serves to deform the tubular wall to the shape with the longitudinally extending helical cavity. It may also form the helical portion of the tubing for resisting reduction of the amplitude of the helical centre line, i.e. to help it retain its shape. The elongate member may advantageously therefore serve a dual function and simplify manufacture.

As with the previously described manufacturing methods, it will generally be undesirable for the cross-sectional shape of the tubular wall to be distorted, for example flattened, during tensioning. Preferably, therefore, the tubular wall is reinforced to assist it in maintaining its cross-sectional shape during tensioning of the elongate member. The reinforcement may be integral with or adherent to the tubular wall, for example comprising a helical winding with a large helix angle, as is known for example from GB 2298577. Alternatively, or additionally, it may be desirable to provide reinforcement in the form of internal support for the tubular wall during tensioning of the elongate member. A flexible rod or tube or a spring may be inserted into the tubular wall to provide internal support and removed after the desired geometry has been at least partly retained.

A preferred cross-sectional shape of the longitudinally extending helical cavity is substantially circular. If reinforcement is provided, it may then help the tubular wall to keep to this shape.

The step of at least partially retaining the tubular wall in a shape with a longitudinally extending helical cavity is preferably a thermosetting step. Preferably therefore the materials of the tubular wall and the elongate member are such as to permit thermosetting of the tube in the desired shape. It is preferred for the elongate member to be such that it retains its tension when heated, i.e. it does not soften or melt to the extent that it allows the tubular wall to straighten out. The elongate member preferably also bonds to the tubular wall when heated, for example by melting. Then, when cooling takes place the elongate member is bonded to the tubular wall and holds it in the shape with the longitudinally extending helical cavity. An elongate member made of a biocompatible polymer, e.g. polypropylene, heated to just above its melting point for an appropriate time can provide both the tension retention and the bonding properties.

Alternatively, the elongate member may be of composite construction, including a first material which retains tension when heated and a second material which bonds to the tubular wall. The elongate member may then comprise a tensile element, such as a metal wire, in a sleeve for bonding to the tubular wall. The sleeve may be made of a biocompatible polymer which can soften sufficiently when heated to bond to the tubular wall. The tensile element may if desired be removed from the sleeve after the tubular wall has set in the desired shape. This may be of benefit if the tensile element is not biocompatible.

According to another aspect of the invention, there is provided a method of making a graft, the method comprising providing a generally tubular wall with a helical portion extending longitudinally and circumferentially, the helical portion being less extensible than adjacent portions of the wall, and radially expanding the wall, whereby the helical portion causes the wall to define a longitudinally extending cavity having a centre line following a substantially helical path.

It is preferred in the above method to cause the tubular wall to retain, at least partly, the shape with the longitudinally extending helical cavity. This may be achieved for example by thermosetting.

BRIEF DESCRIPTION OF THE DRAWINGS

Certain preferred embodiments of the invention will now be described by way of example and with reference to the accompanying drawings, in which.

DETAILED DESCRIPTION

Figure 1:
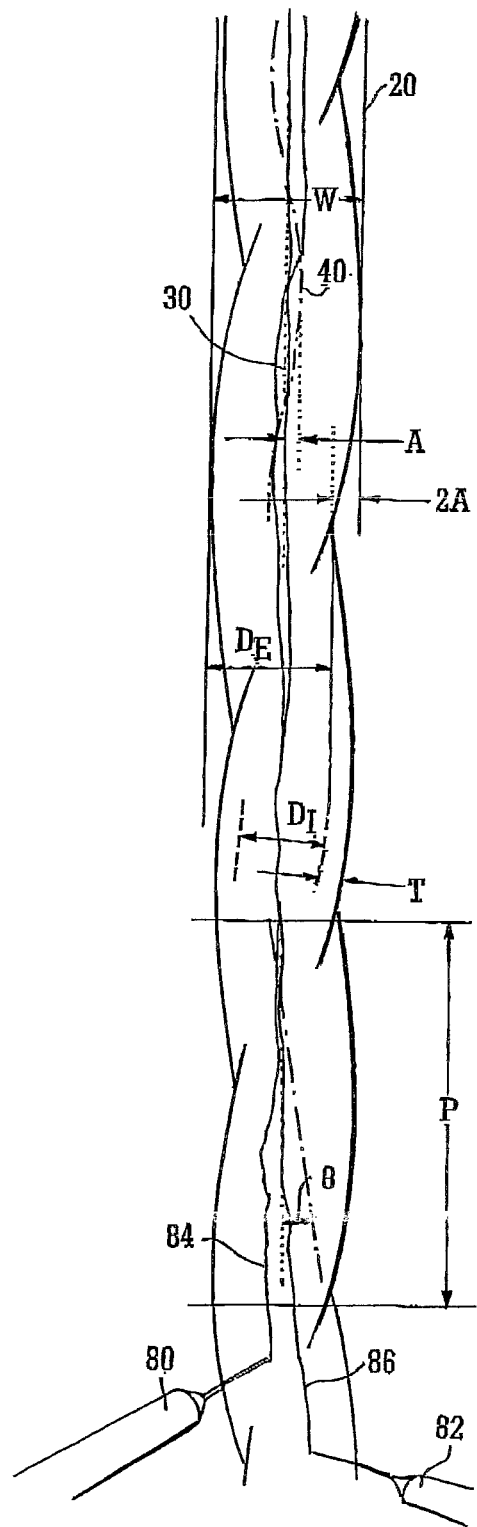
FIG. 1 is an elevation view of a tubing portion in accordance with the invention.

The tubing portion 1 shown in FIG. 1 has a circular cross-section, an external diameter $D_E$, an internal diameter $D_I$ and a wall thickness T. The tubing is coiled into a helix of constant amplitude A (as measured from mean to extreme), constant pitch P, constant helix angle θ and a swept width W. The tubing portion 1 is contained in an imaginary envelope 20 which extends longitudinally and has a width equal to the swept width W of the helix. The envelope 20 may be regarded as having a central longitudinal axis 30, which may also be referred to as an axis of helical rotation. The illustrated tubing portion 1 has a straight axis 30, but it will be appreciated that in alternative designs the central axis may be curved. The tubing portion has a centre line 40 which follows a helical path about the central longitudinal axis 30.

It will be seen that the amplitude A is less than the tubing internal diameter $D_I$. By keeping the amplitude below this size, the space occupied by the tubing portion can be kept relatively small, whilst at the same time the helical configuration of the tubing portion promotes swirl flow of fluid along the tubing portion.

Figure 2:
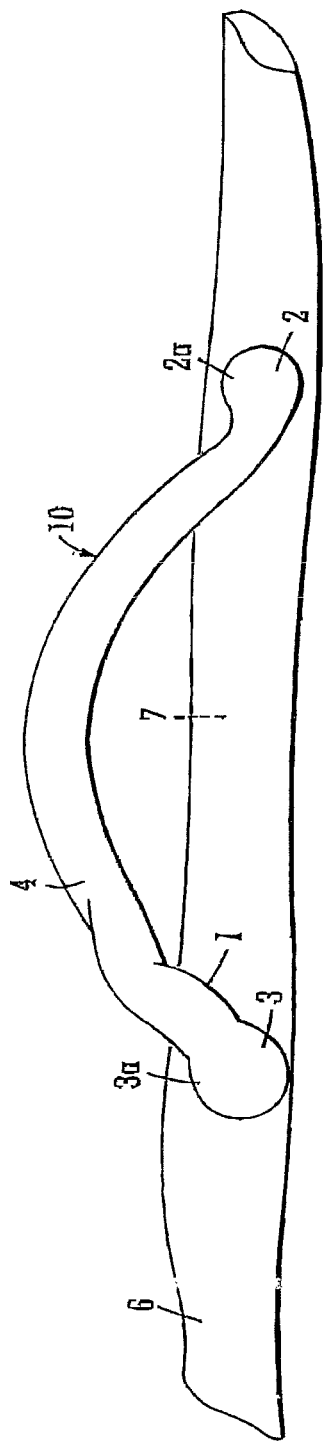
FIG. 2 is a perspective view of a vascular graft.

FIG. 2 shows a prosthesis 10 comprising a length of hollow tubing having an inlet 2 at one end and an outlet 3 at the other end. A generally helical tubing portion 1 is provided at the outlet 3 thereof. The prosthesis has inlet 2a and outlet 3a flaps at its ends which have been surgically fastened by suturing to regions of an artery remote from a blockage 7 in the artery, the prosthesis thus acting as an arterial bypass graft. It could also be surgically connected between an artery and a vein so as a vascular access graft for e.g. renal dialysis.

Blood from the circulatory system can flow from the inlet 2 to the outlet 3 along a hollow interior or lumen 4. The helically formed tubing portion 1 is disposed adjacent to the outlet 3. Its non-planar curvature induces a swirl to the flow to improve circulation by rendering the distribution of wall shear stress relatively uniform and suppressing flow separation and flow instability, and as a result inhibiting the development of vessel pathology. The swirl flow may also resist the build up of intimal hyperplasia at the join and downstream of the join with the vein or artery. The tubing can be made of suitable bio-compatible material and such materials are commercially available and known to those skilled in the art. In order to maintain the tubing open and prevent collapse or kinking it is possible to use a stent or other structural support of plastic, metal or other material internally, externally or integral to the wall of the tubing.

It will be seen that the prosthesis 10 in FIG. 2 is generally arch shaped. This arch may itself be provided in a single plane. If the arch is non-planar then this will also tend to induce swirl flow and it will be desirable to ensure that the swirl flow induced by the non-planar arch is in the same direction as that induced by the helical tubing portion 1.

Figure 3:
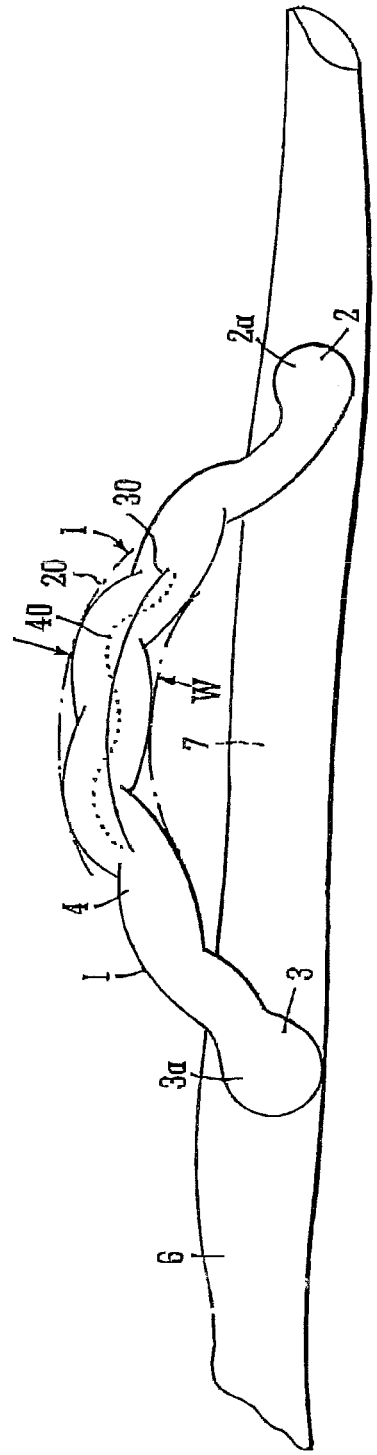
FIG. 3 is a perspective view of another vascular graft.

The arrangement of FIG. 3 is similar to that of FIG. 2, except that the helically formed tubing portion 1 extends substantially the full length of the prosthesis 10. This type of arrangement may simplify manufacture as the tubing could be made in a continuous length which simply has to be cut to appropriate shorter lengths to form prostheses.

Part of the envelope 20 within which the tubing portion 1 is defined is shown in FIG. 3. The swept width W defines the width of the envelope. The longitudinal axis 30 of the envelope is curved, the tubular portion being arch shaped. The centre line 40 follows a helical path about the axis 30.

Figure 4:
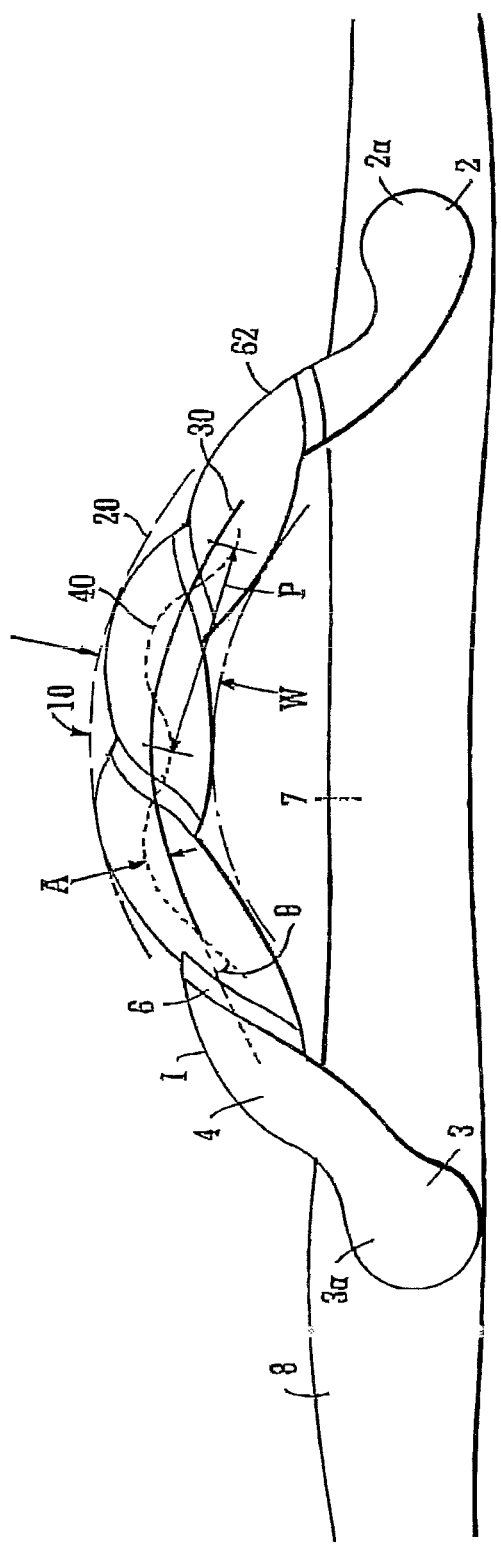
FIG. 4 is a perspective view of a vascular graft.

The vascular graft 10 shown in FIG. 4 has a substantially circular cross-section. The tubing is coiled into a helix of constant amplitude A (as measured from mean to extreme), constant pitch P, constant helix angle θ and a swept width W. The tubing 1 is contained in an imaginary envelope 20 which extends longitudinally and has a width equal to the swept width W of the helix. The envelope 20 may be regarded as having a central longitudinal axis 30, which may also be referred to as an axis of helical rotation. The illustrated tubing 1 has a curved axis 30. The tubing has a centre line 40 which follows a helical path about the central longitudinal axis 30.

The tubing 1 has a helical portion 6 extending longitudinally and circumferentially with the same pitch as pitch P of the helical centre line 40. The helical portion 6 consists of a strip of material secured to the wall 62 of the tubing 1.

The tubing 1 has an inlet 2 at one end and an outlet 3 at the other end. The tubing has inlet 2a and outlet 3a flaps at its ends which have been surgically fastened by suturing to regions of an artery 8 remote from a blockage 7 in the artery, the graft 10 thus acting as an arterial bypass graft. It could also be surgically connected between an artery and a vein so as to serve as a vascular access graft for e.g. renal dialysis.

Blood from the circulatory system can flow from the inlet 2 to the outlet 3 along a hollow interior or lumen 4 of the graft 10. It operates in a manner similar to the graft of FIG. 3, having a non-planar curvature and resist the development of pathology. The swirl flow may also resist the build up of intimal hyperplasia at the join and downstream of the join with the vein or artery.

The tubing 1 may be made of various materials. Suitable bio-compatible materials are commercially available and known to those skilled in the art. One suitable material is polyester. A knitted polyester yarn such as polyethylene terephthalate, known as Dacron (trade mark) is a particular example. The helical portion may be made of the same material or another material, such as polypropylene. The helical portion, rather than being a separate strip secured to the wall 62 of the tubing 1, may be an integral part thereof, for example by being knitted or stitched in to the wall.

Figure 5:
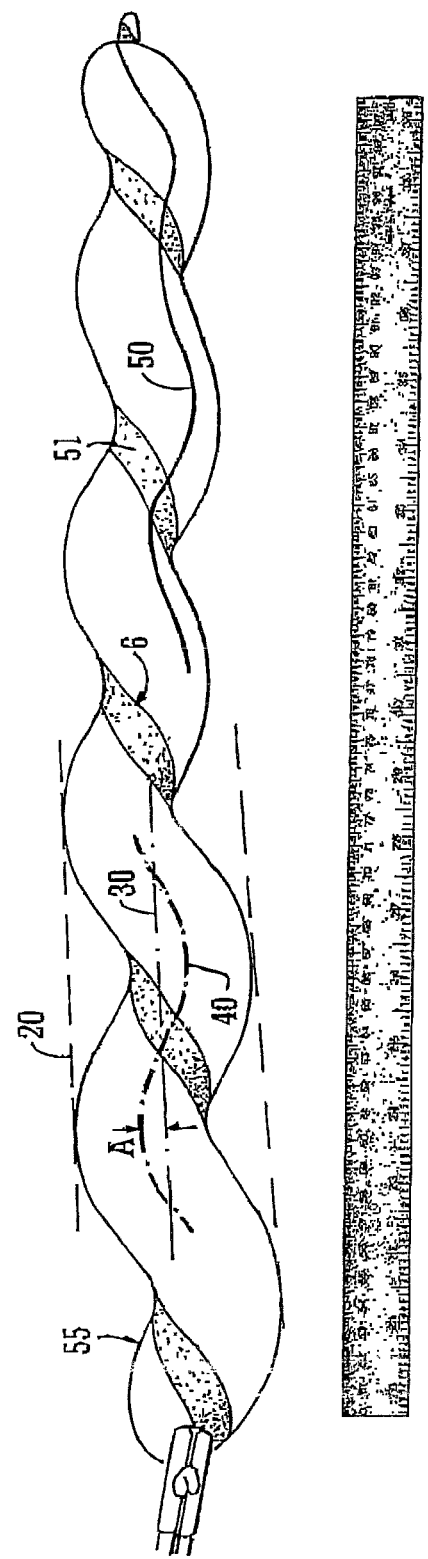
FIG. 5 is a view of an experimental balloon.

FIG. 5 shows the result of an experiment carried out on a toy balloon 55. The balloon was of the elongated type. It was supported, without being inflated, on a cylindrical rod and a plastic strip 51 cut from another balloon was glued onto the outside of the supported balloon to form a longitudinally and circumferentially extending helical strip 6. A straight line 50 was drawn along the balloon. After the glue had set, the balloon was inflated and the inflated balloon is shown in FIG. 5.

It will be seen that the inflated balloon 55 has a helical lumen. As with the tubing for fluid flow, it has a helical centre line 40, which follows a helical path about a longitudinal axis 30. The longitudinal axis is at the centre of an imaginary cylindrical envelope 20 within which the balloon is contained. The amplitude A of the helix is shown in FIG. 5.

It will be noted that after inflation the straight line 50 adopts a wave shape which remains consistently along the same side of the balloon, so that the entire line 50 remains visible in the elevation view of FIG. 5.

The balloon of FIG. 5 starts as a cylindrical membrane with a helical portion which is of greater (in this case double) wall thickness than the rest of the balloon. During inflation the thicker helical portion will tend to resist extension in all directions, including circumferential and longitudinal directions, thereby influencing the shape of the expanded balloon. Instead of adopting the normal cylindrical shape, the balloon forms a shape with a helical centre line 40.

The balloon is internally pressurised in a manner to some extent analogous with the internal pressurisation of the tubing of the preferred embodiments of the invention. The helical portion causes what would otherwise be a cylindrical shape to adopt and maintain helical geometry. A similar effect is obtained by the helical portion of the tubing for body fluid flow, wherein the helical portion tends to help the tubing maintain its helical longitudinal cavity, i.e. to resist "straightening out".

A tubing having a wall defining a longitudinally extending cavity having a centre line following a substantially helical path was manufactured as follows.

A pair of flexible cylindrical tubes made from polyester were internally supported by insertion of respective closely fitting coiled springs. The two supported tubes were then positioned adjacent to each other and twisted around each other. The pair of tubes were thermoset in the twisted configuration by immersion in hot water followed by removal and cooling. The tubes were separated and the coil springs removed. The internal geometry of each tube so formed consisted of a longitudinally extending cavity having a centre line following a substantially helical path. One of the tubes was subjected to internal pressurisation by insertion of a cylindrical balloon which was then gently inflated. Because of the flexible nature of the material forming the tube, the effect of the internal pressurisation was to straighten out the helix, in that the pitch was increased and the amplitude decreased.

Such a straightening out effect is however resisted by the use of a helical portion applied to the tube, as described herein. The helical portion is applied to each of the tubes before they are deformed and thermoset as described above. During the step of twisting the two tubes around each other, they are positioned so that their respective helical portions lie in contact with each other.

A similar method was used to manufacture another tubing having a wall defining a longitudinally extending cavity with a centre line following a substantially helical path. In this case, the tubing was made of expanded polytetrafluoroethylene (ePTFE). Biocompatible tubing of this type is available for use as vascular prostheses, for example from Vascutek Limited or Boston Scientific Corporation.

Figure 6:
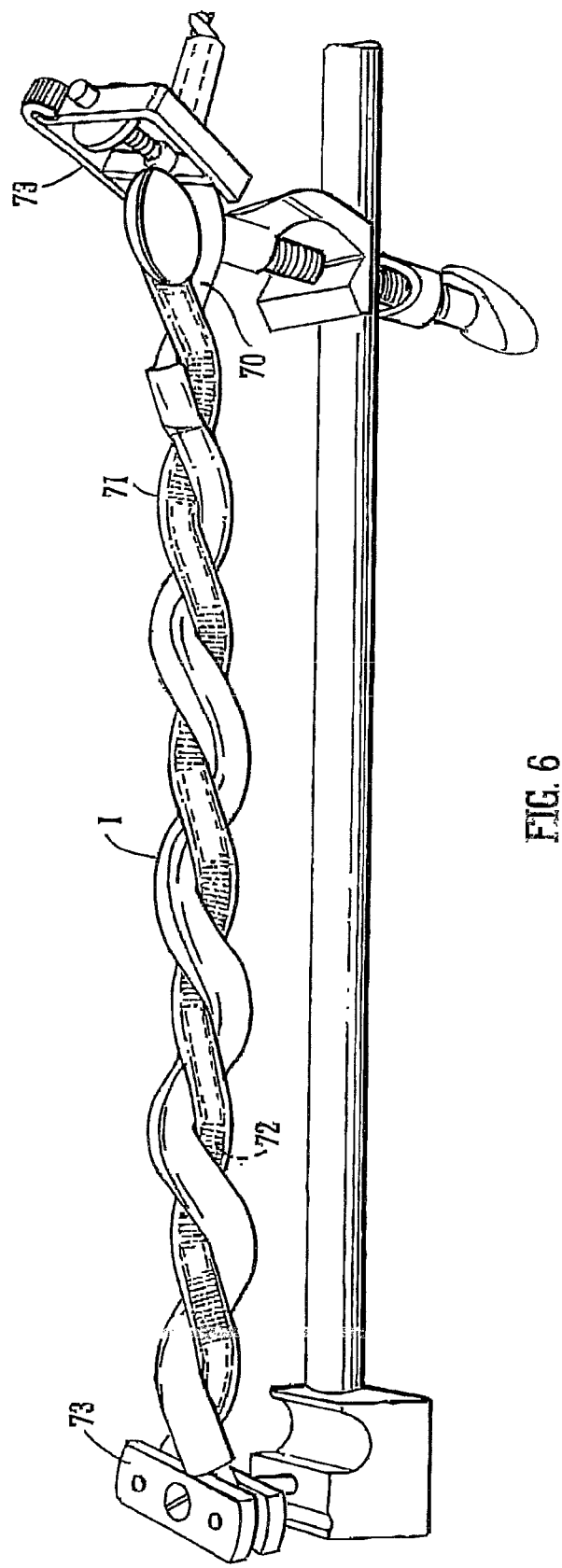
FIG. 6 is a view of a vascular graft twisted with a flexible member during manufacture.
Figure 7:
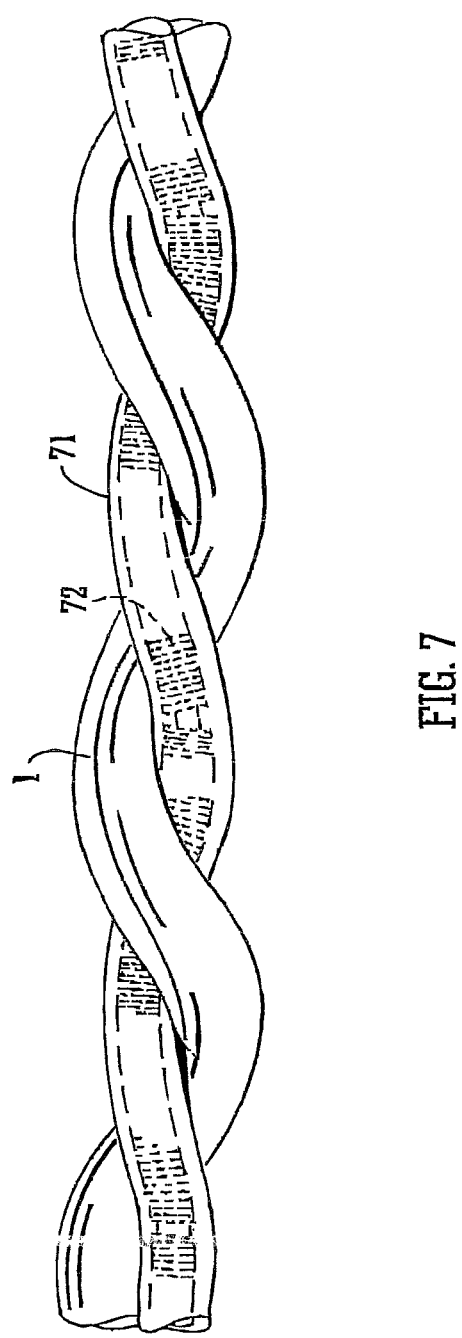
FIG. 7 is a view of part of the vascular graft of FIG. 6, to an enlarged scale.
Figure 8:
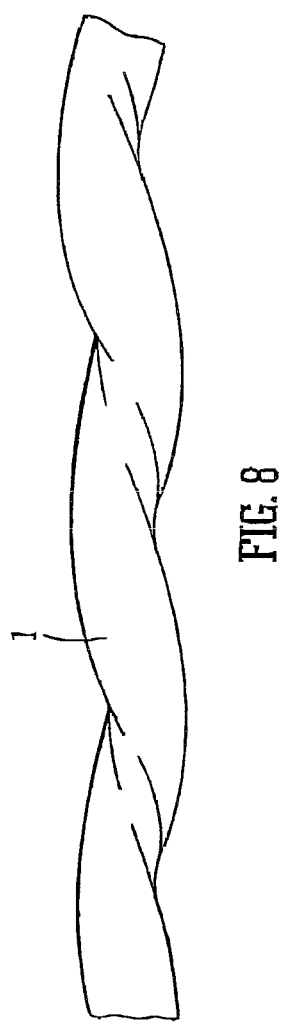
FIG. 8 is a view of the vascular graft made by the method shown in FIGS. 6 and 7.

Referring to FIGS. 6 and 7, a length of ePTFE tubing 1 was internally supported by insertion of a length of silicone rubber tubing 70. A length of polyvinyl chloride (PVC) tubing 71 was internally supported by insertion of a closely fitting coiled spring. The two supported tubes were positioned adjacent to each other and twisted around each other. The support tube 70 was clamped at each end by respective clamps 73, these clamps also serving to clamp the ends of the PVC tube 71. The internally supported, twisted and clamped tubes were placed in an oven at 180° C. for 5 minutes and then cooled by immersion in water at room temperature. The tubes were separated and the support tube 70 was removed from the tubing 1. The tubing was thermoset in a twisted configuration, as seen in FIG. 8. Although the amplitude of the helix was reduced compared to the amplitude during the heating step, the tubing had the desired longitudinally extended cavity with a centre line following a substantially helical path.

A test was carried out on the tubing 1 to investigate its ability to maintain its helical geometry. One end was clamped and the other end was connected to a water supply at a pressure head of 1.5 meters (roughly equal to blood pressure). It was observed that the helical geometry was maintained after 24 hours.

Figure 9:
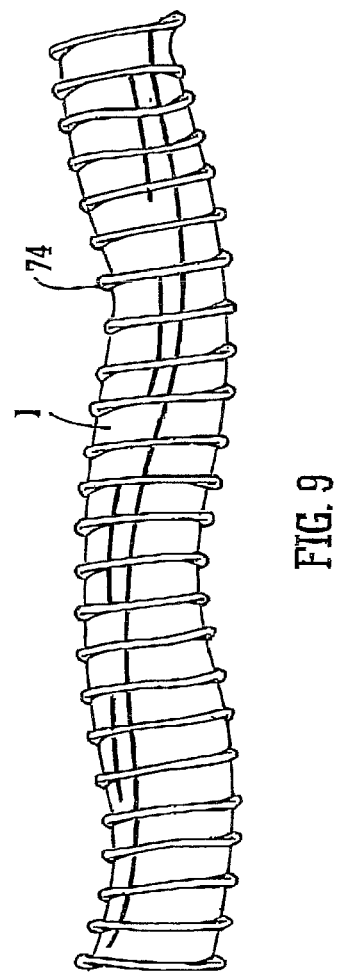
FIG. 9 is a view of another vascular graft made by the same method.

FIG. 9 shows another length of ePTFE tubing manufactured using the above method. In this case the tubing 1 used at the start was of the armoured type, having an external helical winding 74 with a large helix angle (close to 90°). This type of tubing is used in prostheses subject to external bending forces, for example going across joints such as the knee, and the helical winding serves to help maintain a circular cross-section. It will be noted that such armoured tubing was also successfully modified to have a longitudinally extending cavity with a centre line following a substantially helical path.

Figure 10A:
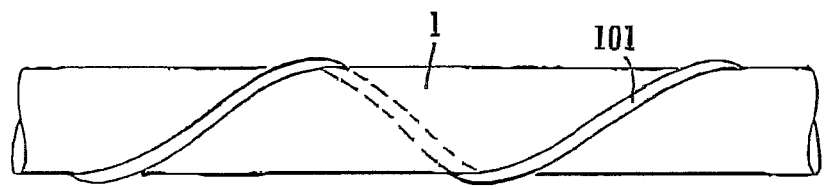
FIGS. 10a and 10b are views illustrating another method of manufacturing a graft.
Figure 10B:
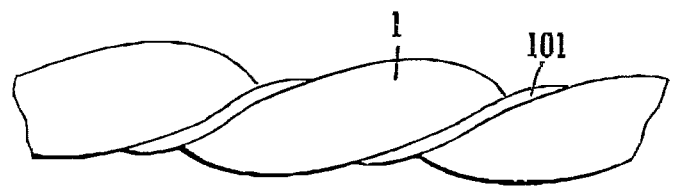

In an alternative manufacturing method, only one tube, rather than two, is used. The method is described with reference to FIGS. 10a and 10b. An elongate member, in the form of a thread 101, is helically wound round an initially cylindrical tube 1. As seen in FIG. 10a, the thread 101 is arranged helically along the tubing so as to extend longitudinally and circumferentially thereof. The thread is tensioned and causes the tube to distort helically, such that its longitudinally extending cavity has a centre line following a substantially helical path. The pitch is dictated by the pitch of the winding of the thread. The amplitude is dictated by the tension on the thread. The tension, and hence the helical deformation, is maintained by securing the ends of the thread, for example to a suitable rig. The deformed tube is then heated so as to thermoset and so as to soften the thread sufficiently for it to bond to the tube. The thread therefore serves the purposes first of creating the helical geometry during the tensioning step, and later of helping to retain that geometry when the tube is used and internally pressurised by e.g. arterial pressure. As with other methods described herein, the tubing may be externally or internally supported during this process.

In a preferred method a knitted polyester yarn such as polyethylene terephthalate, known as Dacron (trade mark), is a suitable material for the tube, whilst the elongate member may be polypropylene. The tube may be externally supported with helically wound (with a very large helix angle, close to 90°) polypropylene. With these materials the heating step is carried out by heating the tube and tensioned thread in an oven at 140° C.

Figure 11A:
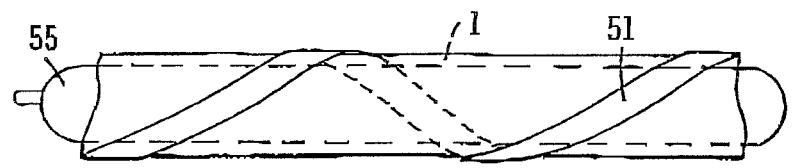
FIGS. 11a and 11b are views illustrating another method of manufacturing a graft.
Figure 11B:
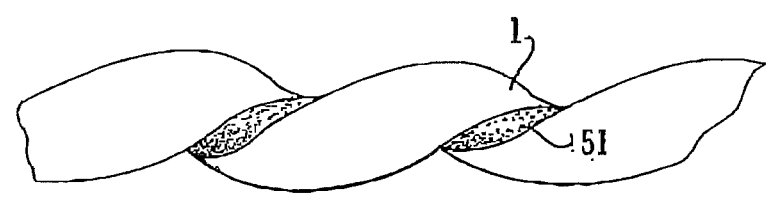

In another alternative manufacturing method using only one tube, the tube is initially cylindrical, with a helical portion extending along its wall. The method is described with reference to FIGS. 11a and 11b. In this method, tubing 1 is provided with a reinforcing strip 51 adhered to its outside surface so as to extend longitudinally and circumferentially of the tubing. An inflatable device 55 is located inside the tubing. The inflatable device is inflated in order to expand the tubing. During this process the helically arranged strip 51 causes the tubing to expand to a shape having a longitudinal, helical cavity, as seen in FIG. 11b. The tubing adopts the helical geometry in the same manner as the balloon shown in FIG. 5. The tubing is thermoset in this condition and allowed to cool, in order to retain the desired helical shape. The material of the inflatable device 55 is chosen to withstand the elevated temperature required to thermoset the tubing.

The helical portion, in the form of strip 51, thus serves the purposes first of creating the helical geometry during the inflation step, and later of helping to retain that geometry when the tube is used and internally pressurised by e.g. arterial pressure.

Another method of making a graft is described with reference to FIGS. 12a to 12e. This method involves the use of a helical mandrel.

Figure 12A:
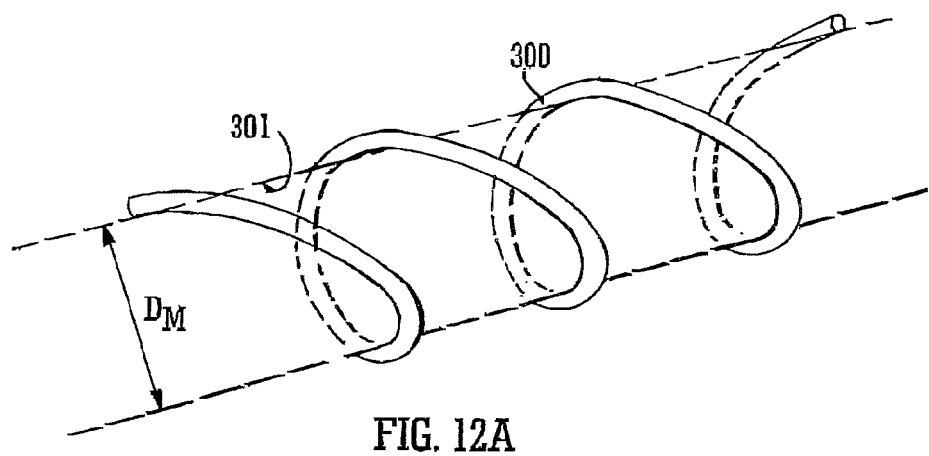
FIGS. 12a to 12e are views illustrating a method of manufacturing a graft.

FIG. 12a is a schematic illustration of a helical mandrel for use in this method. The mandrel consists of a rigid rod 300, shaped into a helix. The mandrel extends longitudinally and circumferentially around a cylindrical space which defines a core 301 of the mandrel. In the embodiment shown, the pitch and the amplitude of the helix are constant along the length of the mandrel, but they may vary if desired.

Figure 12B:
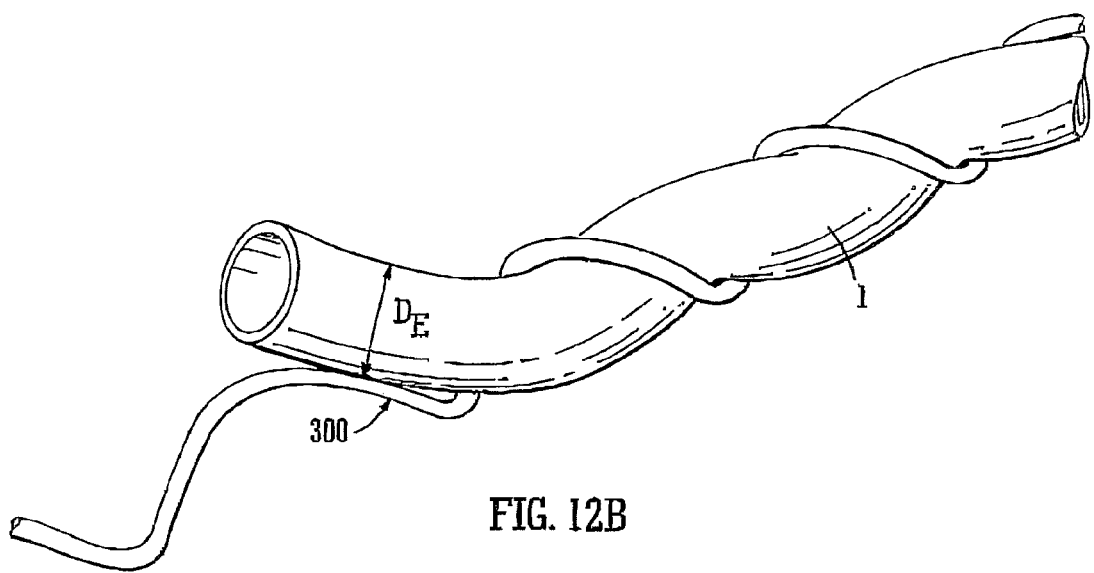

In order to form a helical portion, a length of straight flexible tube 1, whose external diameter $D_E$ is greater than the internal diameter $D_M$ of the core of the mandrel, is fed generally along the core of the mandrel, as shown in FIG. 12b. Because the tube is wider than the space inside the mandrel, it is forced to adopt a helical form. The tube may be externally or internally supported to retain its cross-sectional shape during this process.

Figure 12C:
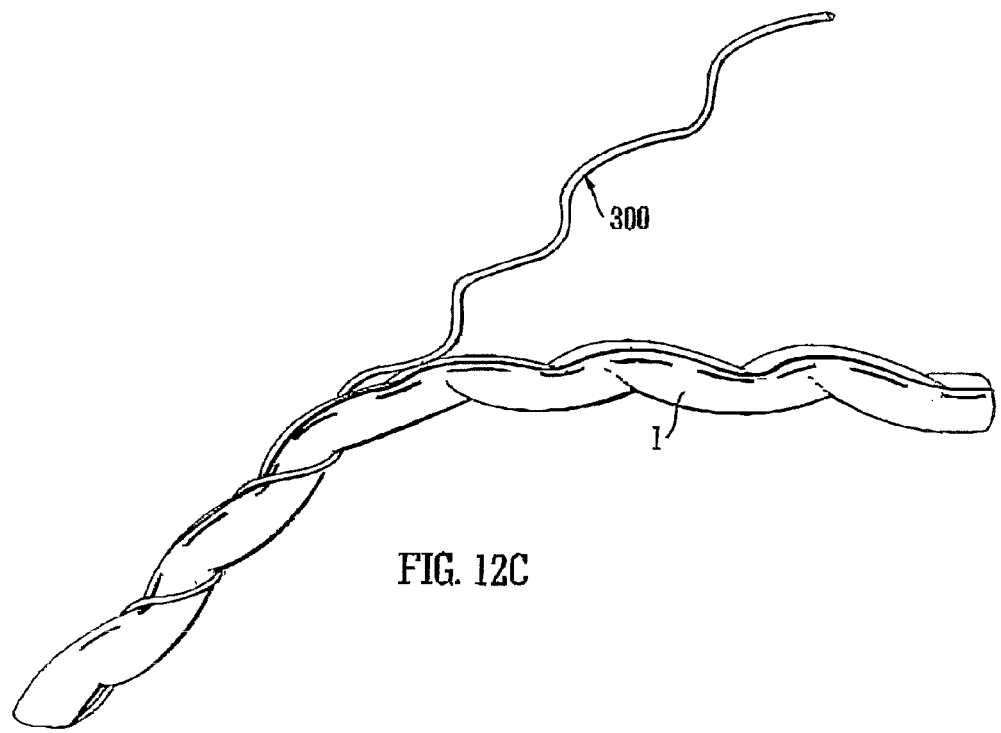
Figure 12D:
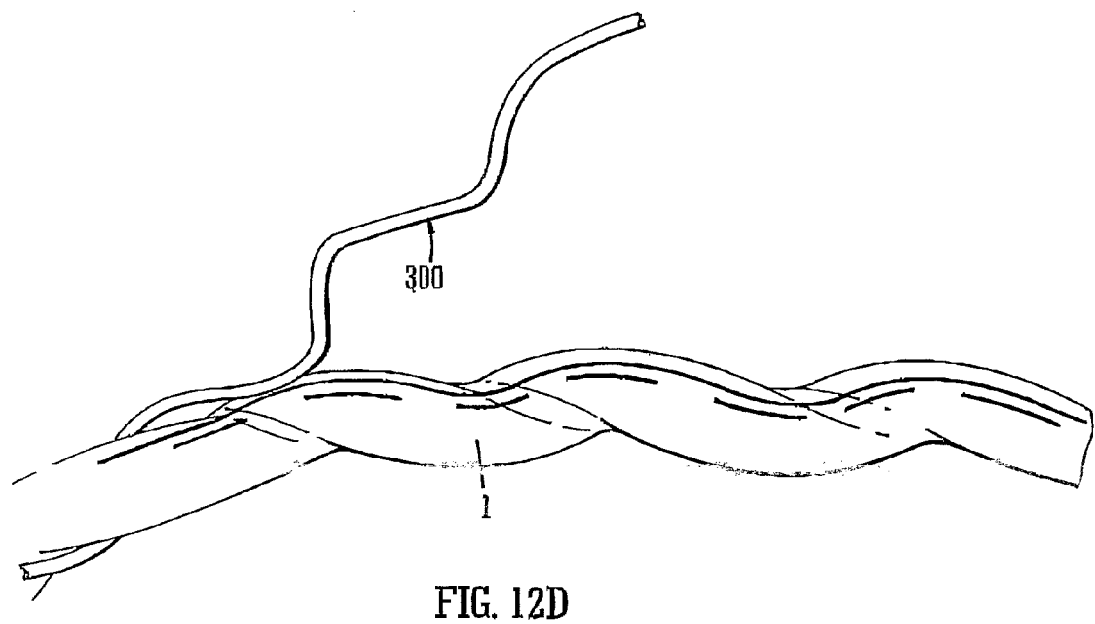

After being treated to make it retain its helical shape, e.g. by thermosetting, the tube is removed from the mandrel, as shown in FIGS. 12c and 12d.

As can be seen, the pitch of the helical portion is the same as the pitch of the mandrel, subject to some possible relaxation of the tube when removed from the mandrel. The amplitude of the helical portion will be determined by the external diameter of the tube and the internal diameter of the core of the mandrel.

The above description concerns a batch processing method for forming the helical tubing, but this method also lends itself to continuous operation. A continuous length of flexible tube can be drawn through a comparatively short length of mandrel, and can be treated to retain its shape as it is drawn through (for example, by heating and then cooling a tube formed from a thermosetting resin).

Experiment has shown that the tube rotates relative to the mandrel when it is drawn through in this way. Thus, some form of lubrication may be required to enable smooth functioning of the process.

Figure 12E:
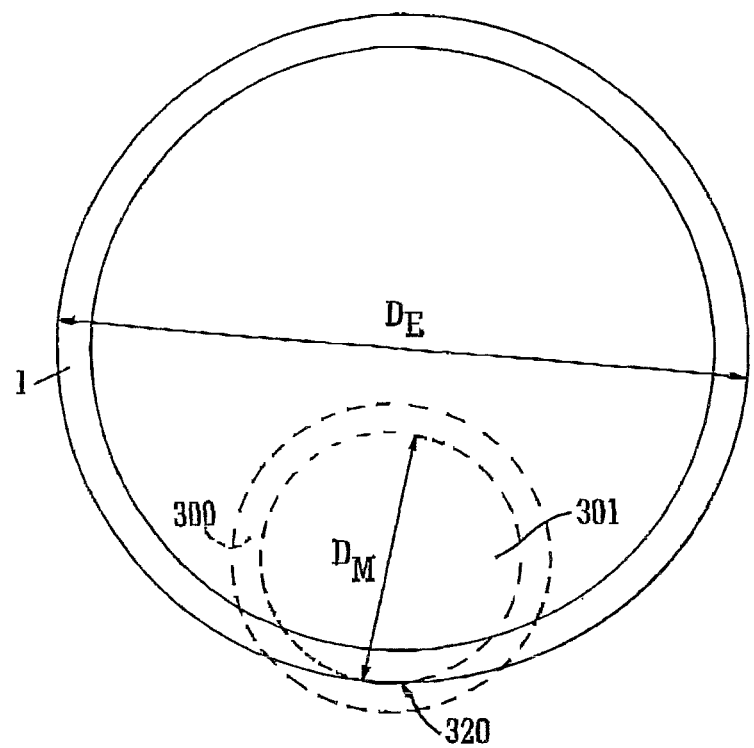

FIG. 12e is a schematic cross-section through the tube and the mandrel as the tube is drawn. It will be seen that the mandrel contacts the outside of the tube, and so the mandrel can be supported from below (at 320) without interfering with the drawing process.

The mandrel can be formed in any suitable manner, and the method of forming the mandrel will depend to a large extent on the size of the tubes being treated. The mandrel could be formed by winding a rod around a member with a circular cross-section, or it may be made by machining, for example using a CNC milling machine.

Figure 13A:
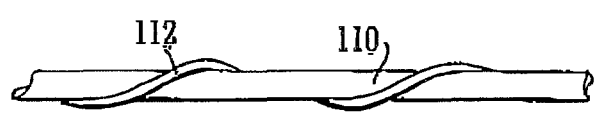
FIGS. 13a and 13b are views illustrating another method of manufacturing a graft.
Figure 13B:
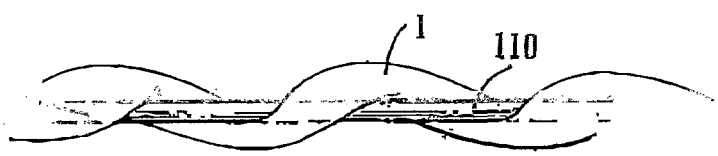

Another method of making a graft is described with reference to FIGS. 13a and 13b. FIG. 13a shows a straight steel rod 110 held in tension between two clamps (not shown). A soft steel wire 112 has been wound on to the steel rod in a helical manner, i.e. to extend longitudinally and circumferentially of the rod. The wire 112 is secured in place by silver solder. The wire 112 forms a guide showing where a tubing 1 is to be wound around the rod 110, which acts as a mandrel. By using the wire 112 as a guide, the pitch (or helix angle) of the tubing when wound onto the rod is predetermined.

The tubing is then heated and cooled in order to thermoset it. It is separated from the rod and when it separates it "relaxes" whereby its helical amplitude reduces. In this example, the tubing is made of ePTFE.

EXAMPLE 1

Experiments were carried out using polyvinyl chloride tubing with a circular cross-section. Referring to the parameters shown in FIG. 1 the tubing had an external diameter $D_E$ of 12 mm, an internal diameter $D_I$ of 8 mm and a wall thickness T of 2 mm. The tubing was coiled into a helix with a pitch P of 45 mm and a helix angle θ of 8°. The amplitude A was established by resting the tubing between two straight edges and measuring the space between the straight edges. The amplitude was determined by subtracting the external diameter $D_E$ from the swept width W:

$$2A = W - D_E$$

So:

$$A = \frac{W - D_E}{2}$$

In this example the swept width W was 14 mm, so:

$$A = \frac{W - D_E}{2} = \frac{14 - 12}{2} = 1 \text{ mm}$$

As discussed earlier, "relative amplitude" $A_R$ is defined as:

$$A_R = \frac{A}{D_r}$$

In the case of this Example, therefore:

$$A_R = \frac{A}{D_r} = \frac{1}{8} = 0.125$$

Water was passed along the tube. In order to observe the flow characteristics, two needles 80 and 82 passing radially through the tube wall were used to inject visible dye into the flow. The injection sites were near to the central axis 30, i.e. at the "core" of the flow. One needle 80 injected red ink and the other needle 82 blue ink.

Figure 14:
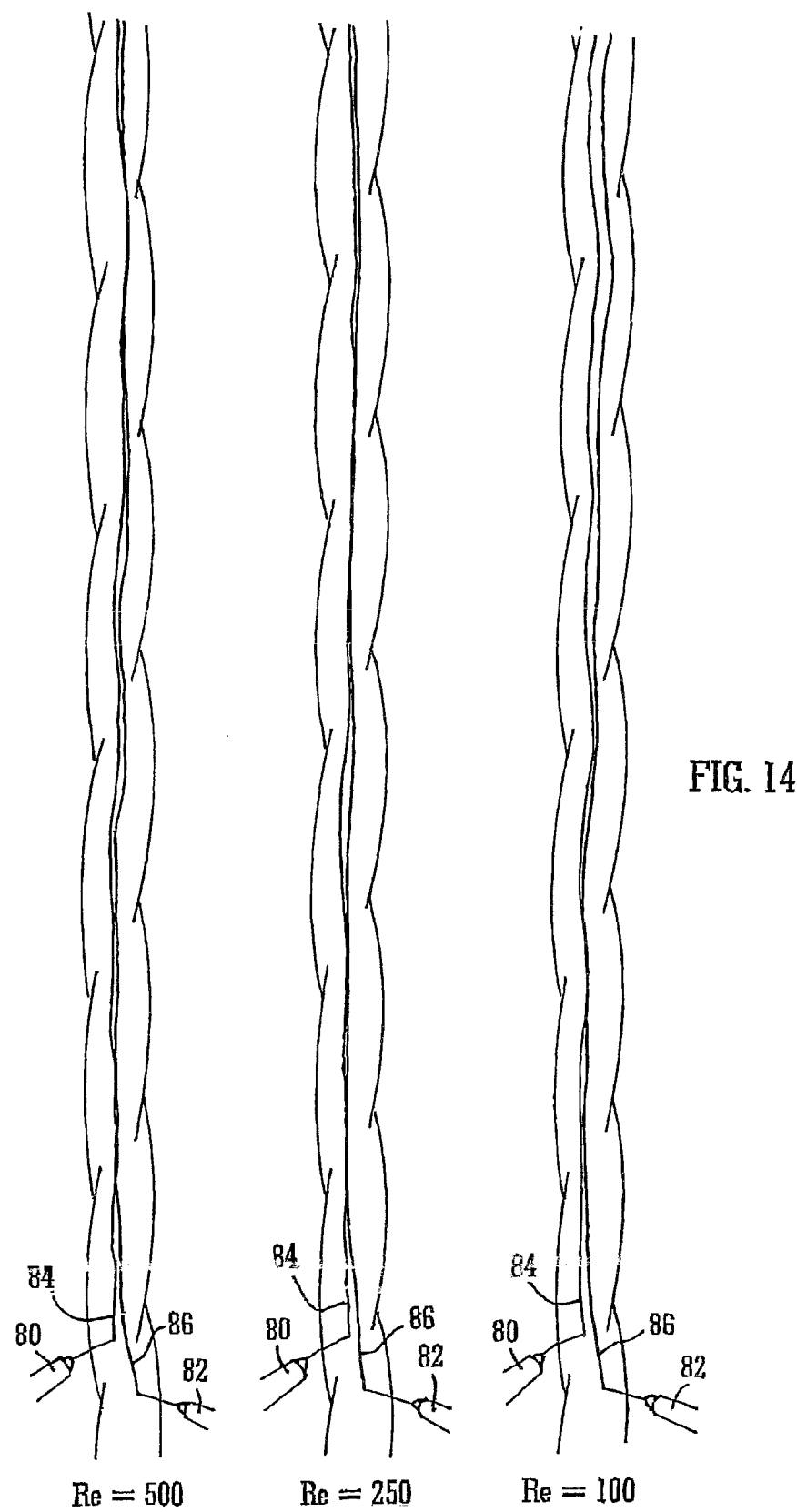
FIG. 14 shows elevation views of tubing portions used in experiments.

FIG. 14 shows the results of three experiments, at Reynolds numbers $R_E$ of 500, 250 and 100 respectively. It will be seen in all cases that the ink filaments 84 and 86 intertwine, indicating that in the core there is swirl flow, i.e. flow which is generally rotating.

EXAMPLE 2

Figure 15:
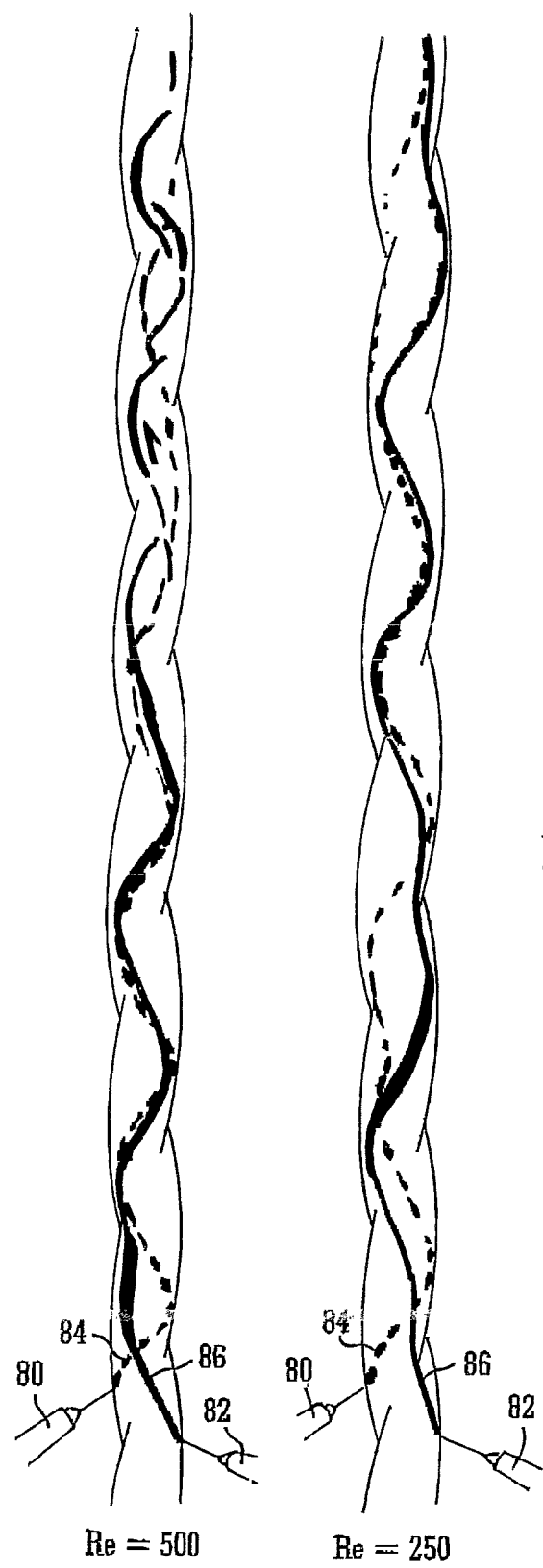
FIG. 15 shows elevation views of tubing portions used in further experiments.

The parameters for this Example were the same as in Example 1, except that the needles 80 and 82 were arranged to release the ink filaments 84 and 86 near to the wall of the tubing. FIG. 15 shows the results of two experiments with near-wall ink release, with Reynolds numbers $R_E$ of 500 and 250 respectively. It will be seen that in both cases the ink filaments follow the helical tubing geometry, indicating near-wall swirl. Furthermore, mixing of the ink filaments with the water is promoted.

It will be appreciated that this invention, in its first aspect, is concerned with values of relative amplitude $A_R$ less than or equal to 0.5, i.e. small relative amplitudes. In a straight tubing portion both the amplitude A and the relative amplitude $A_R$ equal zero, as there is no helix. Therefore, with values of relative amplitude $A_R$ approaching zero, the ability of the tubing portion to induce swirl will reduce. The lowest workable value of relative amplitude $A_R$ for any given situation will depend on the speed of flow and the viscosity and density of the fluid (i.e. Reynolds number) and on the pitch (helix angle) and the particular use of the tubing portion. Relative amplitudes of at least 0.05, 0.10, 0.15, 0.20, 0.25, 0.30, 0.35, 0.40 or 0.45 may be preferred.

The various manufacturing methods described herein are not limited to the manufacture of tubing with a relative amplitude equal to or less than 0.5, unless otherwise specified. The methods are considered to be of independent patentable significance and are applicable to the manufacture of tubing with larger amplitudes, whilst also being particularly useful for making tubing of small relative amplitudes.

The invention claimed is:

1. A method of inhibiting flow instability in a graft for biomedical use, the graft comprising flow tubing which is for use in vivo to carry blood and which is made of biocompatible material, the flow tubing having a tubing portion with an internal diameter and defining a flow lumen, wherein the flow lumen of the tubing portion is of circular cross-section, the flow lumen of said tubing portion having a centre line and being substantially free of ribs or grooves, wherein the graft is thermally set such that it retains a twisted shape and the centre line of the flow lumen follows a helical path about a longitudinal axis so as to define a helical center line, the helical center line having a helix angle and a helix amplitude, the helix angle being less than or equal to 45°, and the helix amplitude being less than or equal to one half of the internal diameter of the tubing portion, and wherein the flow tubing is flexible and is capable of adopting a configuration in which the longitudinal axis is curved and the helical center line of the tubing portion follows a helical path about the curved longitudinal axis.

2. A method as claimed in claim 1, wherein the amplitude of the helical center line divided by the internal diameter of the tubing is at least 0.05.

3. A method as claimed in claim 1, wherein the helix angle is less than or equal to 15°.

4. A method as claimed in claim 1, wherein the centre line of the tubing portion follows a substantially helical path about an axis which is curved.

5. A method as claimed in claim 1, wherein the graft further comprises a pharmaceutical coating.

6. A method as claimed in claim 1, wherein the tubing portion comprises a tubular wall which resists reduction of the amplitude of the helical centre line.

7. A method as claimed in claim 1, wherein the graft is thermally shape set.

8. A method as claimed in claim 1, wherein the tubing portion has a wall comprising a helical winding to help maintain a circular cross-section of the flow lumen.

9. A method as claimed in claim 8, wherein the helix angle of the helical winding is larger than the helix angle of the helical centre line of the flow lumen.

10. A method as claimed in claim 1, wherein the graft comprises ePTFE.

11. A method of inhibiting flow instability in a graft for biomedical use, the graft comprising flow tubing which is for use in vivo to carry blood and which is made of biocompatible material, the flow tubing having a tubing portion with an internal diameter and defining a flow lumen, wherein the flow lumen of the tubing portion is of circular cross-section, wherein the graft is thermally set such that it retains a twisted shape and the center line of the flow lumen follows a helical path about a longitudinal axis so as to define a helical center line, the helical center line having a helix angle and, a helix amplitude, the helix angle being less than or equal to 45°, the helix amplitude being less than or equal to one half of the internal diameter of the tubing portion, and the amplitude of the helical centre line divided by the internal diameter of the tubing portion is at least 0.05, and wherein the flow tubing is flexible and is capable of adopting a configuration in which the longitudinal axis is curved and the helical center line of the tubing portion follows a helical path about the curved longitudinal axis.

12. A method as claimed in claim 11, wherein the helix angle is less than or equal to 15°.

13. A method as claimed in claim 11, wherein the center line of the tubing portion follows a substantially helical path about an axis which is curved.

14. A method as claimed in claim 11, wherein the graft further comprises a pharmaceutical coating.

15. A method as claimed in claim 11 wherein the tubing portion comprises a tubular wall which resists reduction of the amplitude of the helical center line.

16. A method as claimed in claim 11, wherein the graft is thermally shape set.

17. A method as claimed in claim 11, wherein the tubing portion has a wall comprising a helical winding to help maintain a circular cross-section of the flow lumen.

18. A method as claimed in claim 11, wherein the helix angle of the helical winding is larger than the helix angle of the helical center line of the flow lumen.

19. A method as claimed in claim 11, wherein the graft comprises ePTFE.

* * * * *